United States Patent [19]

Wanner et al.

[11] 4,431,008
[45] Feb. 14, 1984

[54] ULTRASONIC MEASUREMENT SYSTEM USING A PERTURBING FIELD, MULTIPLE SENSE BEAMS AND RECEIVERS

[76] Inventors: James F. Wanner, R.R. 2, Box 58C, Charlotte, Vt. 05445; Clinton D. Janney, 37 Colonial Sq., Burlington, Vt. 05401

[21] Appl. No.: 391,542

[22] Filed: Jun. 24, 1982

[51] Int. Cl.³ ............................................. A61B 10/00
[52] U.S. Cl. ...................................... 128/660; 73/606
[58] Field of Search ................... 128/660, 663; 73/596, 73/597, 599, 600, 610, 606, 609, 602, 607, 608, 611, 612, 613, 614, 615, 616, 617, 618, 642

[56] References Cited

U.S. PATENT DOCUMENTS 3,771,355  11/1973  Sachs ................................... 128/663
4,059,010  11/1977  Sachs ..................................... 73/596

Primary Examiner—Kyle L. Howell
Assistant Examiner—Deidre A. Foley
Attorney, Agent, or Firm—Eliot S. Gerber

[57] ABSTRACT

A system for the non-invasive inspection of a living organism utilizes two ultrasonic fields, one of which is produced by a perturbing beam transmitting transducer to perturb an internal region of tissue at a focal region which may be subject to movement. The second ultrasonic field consists of a set of ultrasonic beams, constituting a sense beam and reference beams, and which may be portions of a single beam or a plurality of separate beams and which are directed through and near the focal region of the perturbing field before and/or after perturbation. The time of flight differences of the sense beam and reference beams are detected by a plurality, preferably at least three, receiving transducers whose outputs are processed by a digital computer system, interacting with the signal analysis electronics, to derive information concerning the internal tissue of the living organism. The measurement is based upon time of flight differences ("phase differences" for small-angle variances) of each beam which are the timed differences between the times of flight of coherent bursts of ultrasonic waves.

4 Claims, 7 Drawing Figures

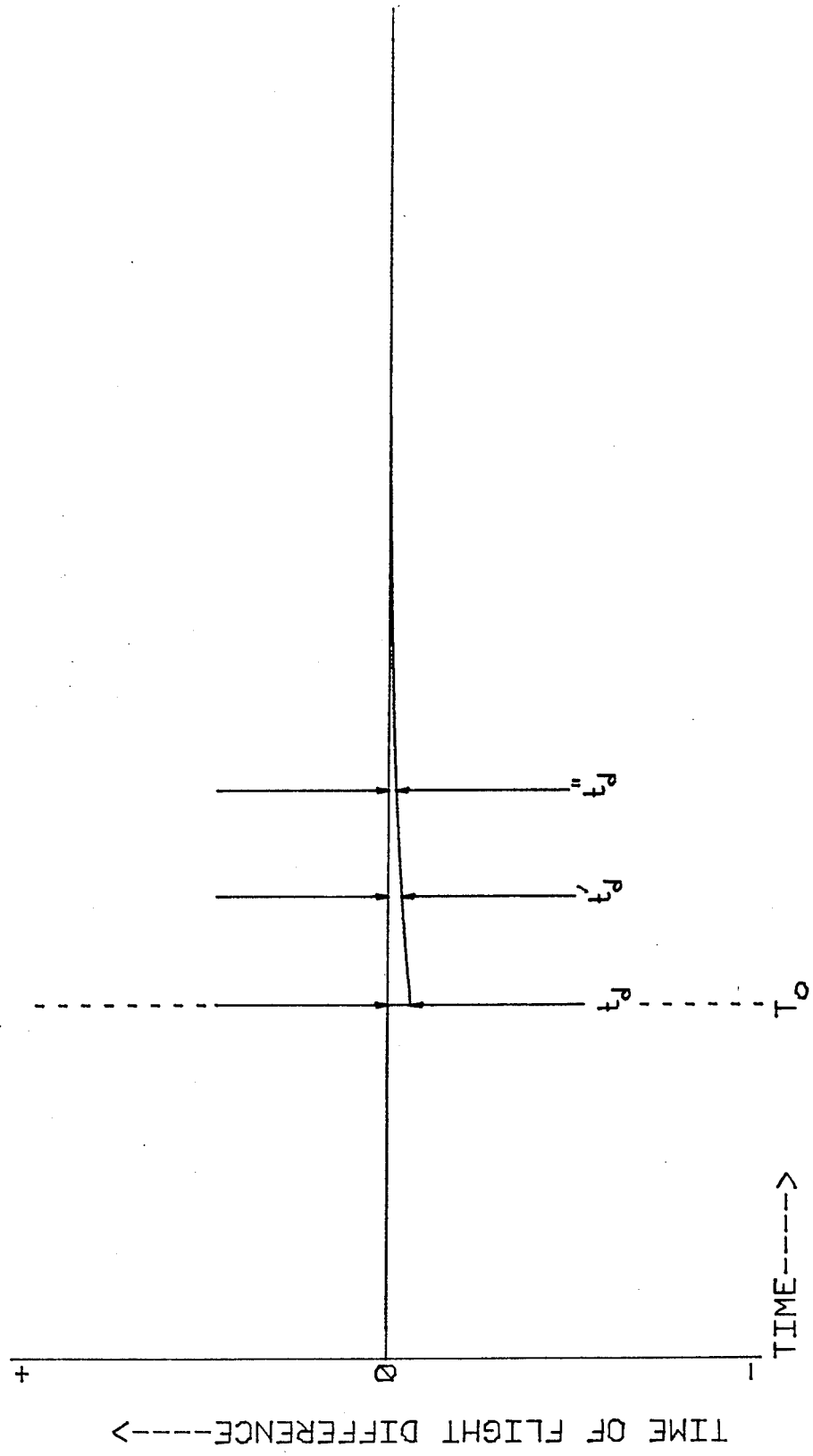
FIGURE 4.1

ULTRASONIC MEASUREMENT SYSTEM USING A PERTURBING FIELD, MULTIPLE SENSE BEAMS AND RECEIVERS

BACKGROUND OF THE INVENTION

At the present time the internal nature of material, such as the tissue of a human patient, may be examined by various means, including X-rays, ultrasonic echo reflections, and radioactive tracer techniques. Each of these techniques has serious limitations. For example, X-rays may be dangerous to unborn children and do not necessarily differentiate adequately between the various types of soft tissues of the body. Echo sounding using ultrasound, while it is sensitive to interfaces between soft tissues—that is what it does detect—cannot be numerically informative because one does not know the nature of the interface which causes the reflections. Ultrasonic reflections from interfaces do not give quantitative information on the nature of soft tissues. Radioactive tracer techniques do give some information on the nature of the metabolism of a tissue by whether the tissue takes up the radioactive tracer or not, but do not give information on the nature of the tissue itself.

In addition, no technique has yet been able to measure the temperature or the perfusion (blood supply) at an internal tissue location without inserting a mechanical device into the patient. Such temperature measurement may be important for certain types of heat treatment (hyperthermia) which have been used to treat some types of tumors (cancer).

The measurement of perfusion (blood supply to a tissue through the capillary network) may be useful for many medical purposes. While measurements have been made using invasive probes such as that of Bowen (Harvard Medical School, reported at 1981 "Summer School on Hyperthermia" at Hanover, New Hampshire, given by the American Association of Physicists in Medicine). No non-invasive method other than that of U.S. Pat. Nos. 3,771,355 and 4,059,010, discussed below, has been suggested.

It has been suggested that the velocity of sound in tissue may be used as a non-invasive way of determining the body temperature, see T. C. Cetas & W. G. Connor, *Thermometry Considerations In Localized Hyperthermia*, MEDICAL PHYSICS, Volume 5, page 79, 1978. However, sending a single sound beam through a patient and measuring the time of flight does not give quantitative information on a specific volume. In principle, it is possible to sweep the beam in an acoustic velocity computed axial tomographic fashion, called Acoustic Time-of-Flight Tomography. However, there are questions as to feasibility of such an approach.

For example, if all tissues examined with an Acoustic Time-of-Flight Tomograph had the dependence of ultrasonic velocity on temperature, such a technique would give an integrated temperature change over the line along which the sound beam is traveling, and not the temperature at any given point; and such a situation could be deciphered. However, since tissues do not all behave in the same fashion (the velocity in fat decreases with temperature while other tissues generally increase their velocity with temperature), it is now generally agreed that no useful information on temperature can be gained in this way.

In U.S. Pat. Nos. 3,771,355 and 4,059,010, both entitled "Ultrasonic Inspection and Diagnosis System" and incorporated by reference herein, an internal focal region ("focal point") of a substance, such as a soft tissue volume of a patient, is perturbed (heated) by ultrasonic waves from a perturbing field which may or may not be collimated or focused, depending on application. An ultrasonic sensing beam consisting of coherent bursts of oscillations is directed through the focal region. A comparison is made of the phase differences which occur in the sensing beam when it is directed through the region before and after the heating. That system, called "TAST" (thermoacoustic sensing technique) is difficult to apply to living organisms (substances) due to movement during testing. If the selected volume (focal region), which is typically a few millimeters across and 5-15 millimeters long, moves from one position before heating to a different position after heating, then the comparison will not be between exactly the same regions and will be inaccurate since it will be comparing different regions of tissue. Such variable inaccuracies constitute "noise" (interference) in the TAST system. Much more importantly, there may be a motion of the tissue which is not in the focal region but which is along the path of the sense beam. If there is motion of the tissue in the path of the sense beam in the TAST system, the time of flight can be changed and lead to large errors, even though this motion does not occur in the focal region. This phenomenon also constitutes system noise (interference).

The internal portions of a living organism, such as a human patient, are almost continually in motion. Some of the motion is rhythmic, for example, that due to the pumping of blood by the heart, or to respiration. Other movement may also be caused by voluntary and involuntary muscle movement (muscle artifact). Such motion, when it occurs along the path of the sense beam in the TAST system, may be a major cause of interference (noise) to the system.

OBJECTIVES AND FEATURES OF THE INVENTION

It is an objective of the present invention to provide an improved two-field non-invasive ultrasonic system for the analysis of temperature, perfusion, and other parameters at internal body locations without adverse effect from movements of the body.

It is a further objective of the present invention to provide such a system which utilizes the capabilities of existing general purpose digital computing systems to operate the system and analyze the data obtained from the tests.

BRIEF DESCRIPTION OF THE DRAWINGS

Other objectives of the present invention will be apparent from the following detailed description of the invention, which description should be taken in conjunction with the accompanying drawings.

In the drawings

DETAILED DESCRIPTION OF THE INVENTION

The original "TAST" system of U.S. Pat. No. 3,771,355 is based on differential measurements of time of flight of collimated sense beam acoustic bursts which are separated in time, i.e., one burst is passed through tissue before, one burst just after the tissue has been perturbed (heated) by a focused ultrasonic field (perturbing field), and possibly other sense beam bursts are passed through the tissue at later times. The sensing technique consists of a comparison of the times of flight (time of transit) of the sensing bursts of the collimated beam.

Figure 1:
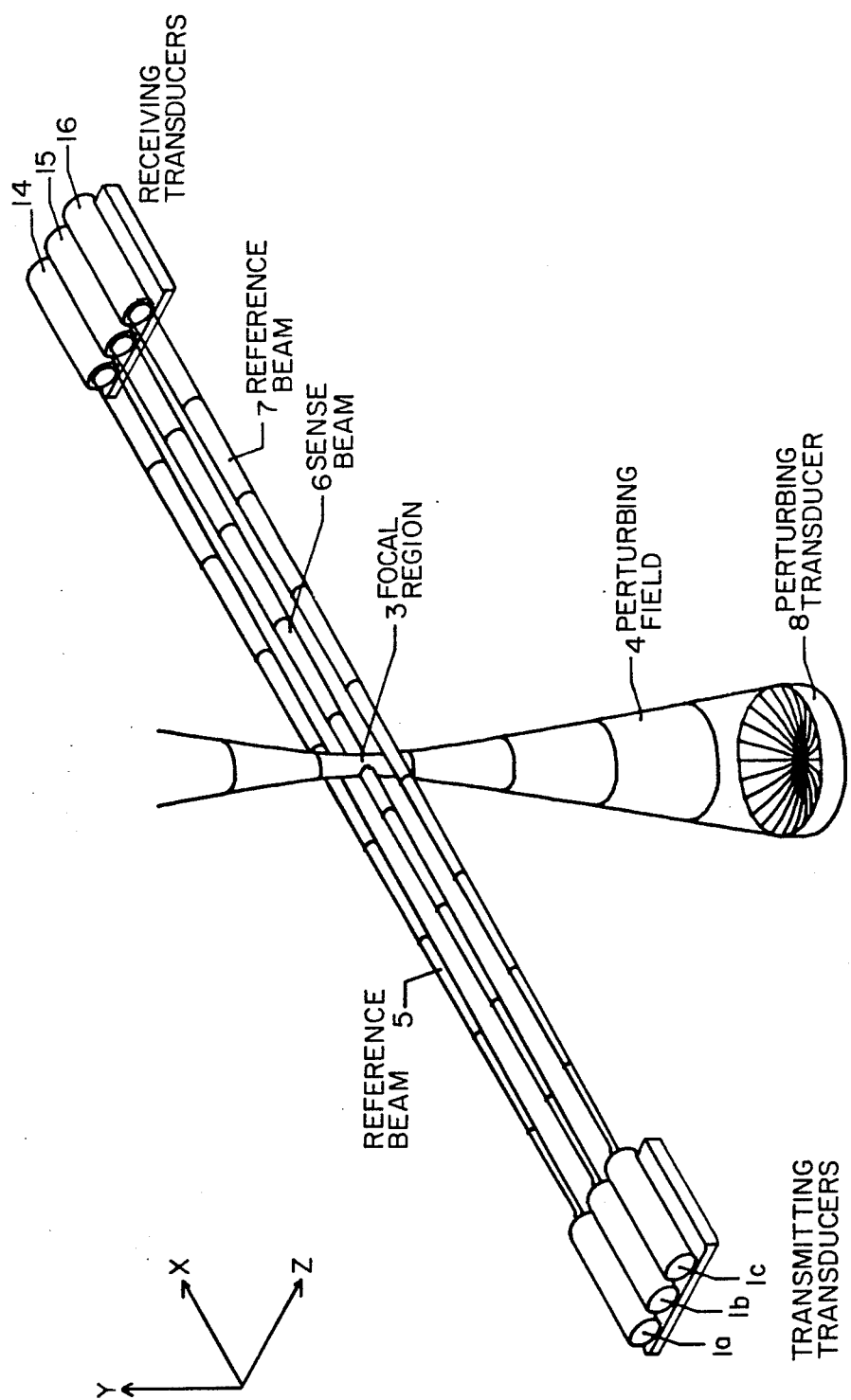
FIG. 1 is a perspective view of a portion of the system of the present invention.

In the improvement of the present invention, as shown in FIG. 1, three sense beam transmitting transducers 1A, 1B, 1C are used to transmit three beams 5,6,7 through the tissue under study. For purposes of savings in cost and simplification of the diffraction patterns involved, three separate transmitting transducers 1A, 1B, 1C and three separate receiving transducers 14,15,16 are used; i.e., the preferred system utilizes three beams 5,6,7 and three separate transmitters and three separate receivers. Alternatively, a single transmitting transducer (10 in FIG. 2) may produce a single wide collimated ultrasonic sensing beam. However, a single large (three-inch) transducer, producing a large field, can cost many times as much because of the difficulty of casting large ceramics.

The transmitting transducers 1A-1C send ultrasound beams through the tissue on both sides of the focal region 3 of the perturbing field 4. The central beam 6 is the "sense beam" as it passes through the focal region (volume) whose tissue characteristic is to be determined. The other beams 5,7 are "reference beams" since they do not pass through that region, but rather pass close by it and thus provide reference information on the motion of the tissue, but not on the perturbation.

In FIG. 1 the sense beam 6 and reference beams 5,7 are shown as three parallel ultrasonic beams. Alternatively, as mentioned above and indicated in FIG. 2, a single beam may be used which is produced by a single transmitting transducer. In FIG. 1 only three acoustic beams are utilized. However, the present invention includes the use of only two beams, one of which is the sense beam through the focal point and the other a single reference beam or an array of more than two reference beams.

The heating (perturbing) field 4 is produced by a second ultrasonic transducer 8 (FIG. 1) focused at the focal region 3. A central receiving transducer 15 is used to receive the sensing burst which has passed through the focal region 3 of the acoustic perturbing field 4. Two additional side receiving transducers 14,16 are mounted immediately to the sides of the central sense beam receiving transducer 15. The side receiving transducers 14,16 receive the reference beams 5,7 which are identical, when transmitted, to the sense beam 6. However, sense beam 6 has passed through the perturbed (heated) focal region and reference beams 5,7 have not been affected by the perturbing field, i.e., they have not passed through the focal region 3.

Comparisons can now be made simultaneously between the times of flight of the sense beam 6 and the reference beams 5,7.

Generally the two reference beams 5,7 will not behave in the same fashion when motions in a living thing occur. For instance, an organ might be moving from side to side, so more of that organ would be moving into one beam while it was moving out of the other and the times of flight of the two beams would be varying in opposite directions rather than in the same direction. However, if one operates the two reference beams 5,7 and the sense beam 6 without the use of the heating field for a period of time, one can fill in parameters in an algorithm which predicts the changes in the time of flight of the sense beam 6 from the changes in time of flight of the two reference beams 5,7. If this process of following the behavior of the times of flight of all three beams continues, the computer which is using the model can make better and better approximations of how the sense beam 6 time of flight is changing on the basis of how the reference beams 5,7 times of flight are changing, until finally there is sifficient precision so that the information from the reference beams is adequate to predict how the sense beam time of flight will vary.

Next, one turns on the perturbing field, heating the focal region 3. The time of flight of the sense beam has been predicted by the algorithm using the data from the two side (reference) beams. One takes the difference between this prediction and the measures time of flight and interpretes this difference as the time of flight difference which would have occurred had there been no motion. This measurement corresponds to that of U.S. Pat. Nos. 3,771,355 and 4,059,010, where no motion was considered.

Figure 2:
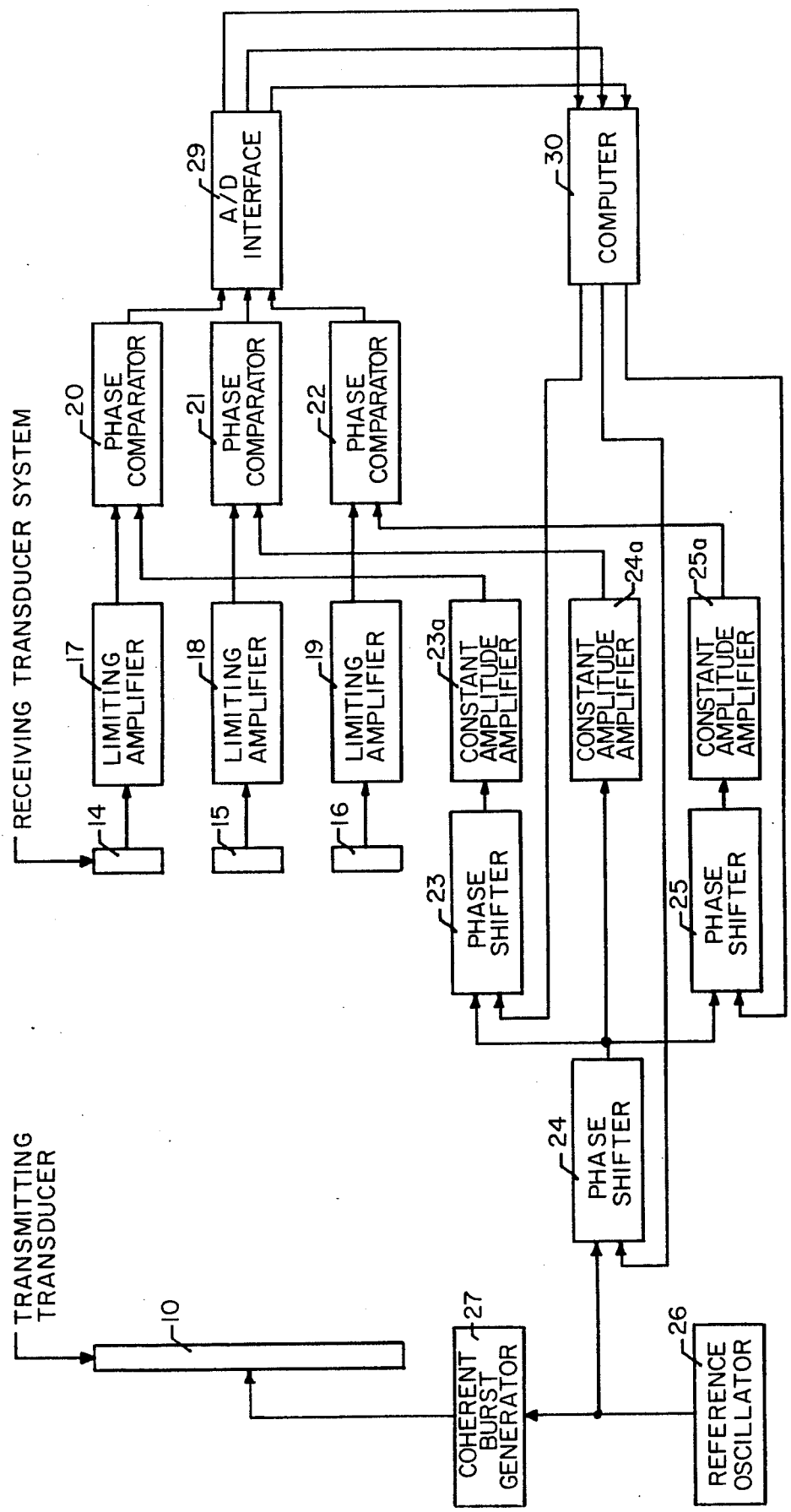
FIG. 2 is a block diagram of a portion of the aforesaid invention.

As shown in FIG. 2, each of the three ultrasonic receiving transducers 14-16 is connected, through a respective limiting amplifier 17-19, to one input of a respective phase comparator 20 22. The other outputs of the three phase comparators are connected, through constant amplitude amplifiers 23A, 24A, 25A, to the separate digitally controlled phase shifters 23-25 and thence to the reference oscillator 26. There is one phase shifter for the received signal from each of the three transducers. Alternatively, and not shown, the system may utilize only one phase shifter in the receiver system and place the other phase shifts in the signal paths that drive the transmiters, i.e., difference phases coming to the various transmitters. In the single transmitting transducer system (10 in FIG. 2) the phase shifting occurs in the signals paths after the acoustic reception instead of before transmission. But in the alternative system all the phase shifting, or the phase shifting for some of the beams, may occur in the signal paths before the transmitters (1A, 1B, 1C in FIG. 1). The amplitudes of each of the three signals are limited by respective limiting amplifiers 14,15,16 while the amplitudes of the reference wave trains are controlled by respective constant amplitude amplifiers 23a, 24a, 25a.

The outputs of the phase comparators 20,21,22 are connected to an analog/digital interface 29 which, in turn, is connected to a digital computer 30 where the time of flight data generated by the system as a whole, including the algorithm, is stored and processed. This computer also uses its control of phase shifters 23-25 as an integral part of its time of flight analysis algorithm. A continuous stream of simultaneous bursts of the sense beam portion 6 and the side beam portions 5,7 are transmitted through the tissue, with a heating field burst interjected at the focal region 3 at an appropriate time.

TIME OF FLIGHT MEASURING TECHNIQUE

The preferred method for detecting phase (time of flight) differences between coherent bursts of ultrasonic waves involves two signal paths from the master oscillator to the double-balanced mixer in the phase comparator for each ultrasonic beam. One of these paths goes through the sensing beam's coherent burst generator, the focal region of the tissue sample and the receiver amplifiers and limiters. The other goes through the digitally controlled phase shifter, and a constant amplitude amplifier. The output amplitude of the signal from the double-balanced mixer is the product of the two input signals, and thus would be affected by their amplitudes as well as their phases. The purposes of both the limiters and the constant amplitude amplifiers is to fix and hold constant the amplitudes of these two signals to that the phase measurement is not interfered with by fluctuations in amplitude of the phase shifter's output (caused by changes in the phase shifter settings) nor by the acoustic absorption of the tissue or other system changes. If the amplitudes of these two signals were not held constant, amplitude fluctuations caused by tissue motion, changes in absorption of the tissue or the changing of the volume being observed might seriously interfere with measurement.

In the phase comparators 20,21,22, the double-balanced mixer's output is first passed through a low-pass filter to remove the acoustic signal frequency and its harmonics, and then integrated during a short time period, which time period is coherent with the acoustic signal and falls during the middle of the received burst. This integration removes the effect of the envelope waveform of the received burst, standardizing the resulting output so that a system constant can be meaningfully defined. The resulting output voltage from the phase comparator represents the phase of the received burst and is converted to digital form for further processing and the comparison of phase shifts by the computer algorithm. The phase comparator consists of the double-balanced mixer, low-pass filter, and gated integrator as described in the above-named "TAST" patents.

The limiters 17,18,19 remove any variations in the amplitude of the received acoustic signal caused by the system or the tissue being examined. The phase information from the tissue is a clipped acoustic frequency waveform having a constant amplitude during the time the burst is being analyzed. Clipping, rather than feedback gain control, is necessary to hold the amplitude constant because the transient nature of the signal being processed prevents the use of the feedback system to control the gain of an amplifier.

Phase shifters tend to vary their output amplitude when they change the phase of the signal they process. Thus, to have a constant amplitude signal from the double-balanced mixer, it is necessary to correct for these variations. Two possibilities exist. One may limit the signal, producing a set of harmonics as with the receiver clipping process. Alternatively, it is possible to generate a constant amplitude sinusoid using a gain controlled amplifier with feedback. In this latter case one makes use of the fact that the phase shifter may be set some time before the acoustic burst's arrival at the receiver, so the transients in the control system have time to die out.

When one feeds one square wave (amplitude limited signal from the acoustic system) and one sinusoid to a double-balanced mixer, the resulting output is the same as it would be if one supplied two sinusoids. The reason for this is that the harmonics from the square wave find no matching components in the sinusoid and thus are multiplied by zeros. In this case the output of the double-balanced mixer, and thus the phase comparator, will be a harmonic function of the phase angle between the two input signals, and must be linearized to be useful in an algorithm. If one uses limiters in both signal paths, two square waves are fed to the double-balanced mixer and its output is a triangular wave. This function, too, must be linearized so that it supplies a monotonic signal to the system's algorithms.

Linearization By Small Angle Approximation

The presently preferred method for linearization uses a small angle approximation. The system first generates a sense beam burst of ultrasonic waves. The small angle approximation algorithm checks to see if the resulting phase comparator output is "close enough" to zero. Close enough may be defined as within the range of output voltage which is generated by one step in the digital phase shifter's output (although this precision may not be necessary for many purposes). If the phase comparator's output is not close enough to zero, the setting of the phase shifter is changed. The algorithm then calls for another sense beam burst and again checks the phase comparator output to see if it is now close enough to zero. If not, it carries out further approximations in this manner until an adequately small value of the output voltage (angle) has been found, i.e., it was close enough to zero.

The final time of flight (phase) measurement of the sense beam 6 consists of three parts, all measured in terms of the acoustic reference frequency. The most significant part is the number of acoustic periods the sense beam 6 requires to cross from transmitter 1b to receiver 15. The next most significant part is the portion of one acoustic period (as measured by the setting of the phase shifter 24) which must be added to the total number of acoustic periods, after the phase shifter has been adjusted by the operation of the small angle approximation. This subdivision of the acoustic period is, of course, only resolved to the level of the digitization of the phase shifter. The least significant part of the time of flight is the subdivision of the steps represented by the digitization of the phase shifter control. This high resolution information can be extracted from the output of the phase comparator once the small angle approximation has operated. One amplifies this "remainder" of the time of transit from the phase comparator and converts it from analog to digital as the least significant (highest resolution) portion of the data.

The phase comparators 20–22, transducers, 1A, 1B, 1C (or alternatively 10 of FIG. 2), 14, 15, 16, coherent burst generator 17, and reference (master) oscillator 26, are preferably of the types described in the aforementioned "TAST" patents. Other devices are commercially available such as the digitally controlled phase shifters 23–25 which may be Model PSD-84-3/22716 produced by Merrimac Industries, West Caldwell, New Jersey, the double-balanced mixer Merrimac Model M109, the constant amplitude amplifier Merrimac Model AGC-3-10. The digital computer may be a PDP8 or PDP11 by Digital Equipment Company, Maynard, Massachusetts, or a suitable microprocessor such as a type 8085 from Intel Co. of Mountain View, California, and A/D interfaces are available from various companies such as Analog Devices Co., Norwood, Massachusetts.

Simple Examples of the Information Obtained

The successive time of flight measurements for the sense beam 6 or either of the side beams 5,7 may be represented, on a graph, as the ordinates of a series of points, the abscissae of which are the $T_o$ times at which the respective times of flight are measured.

Figure 3:
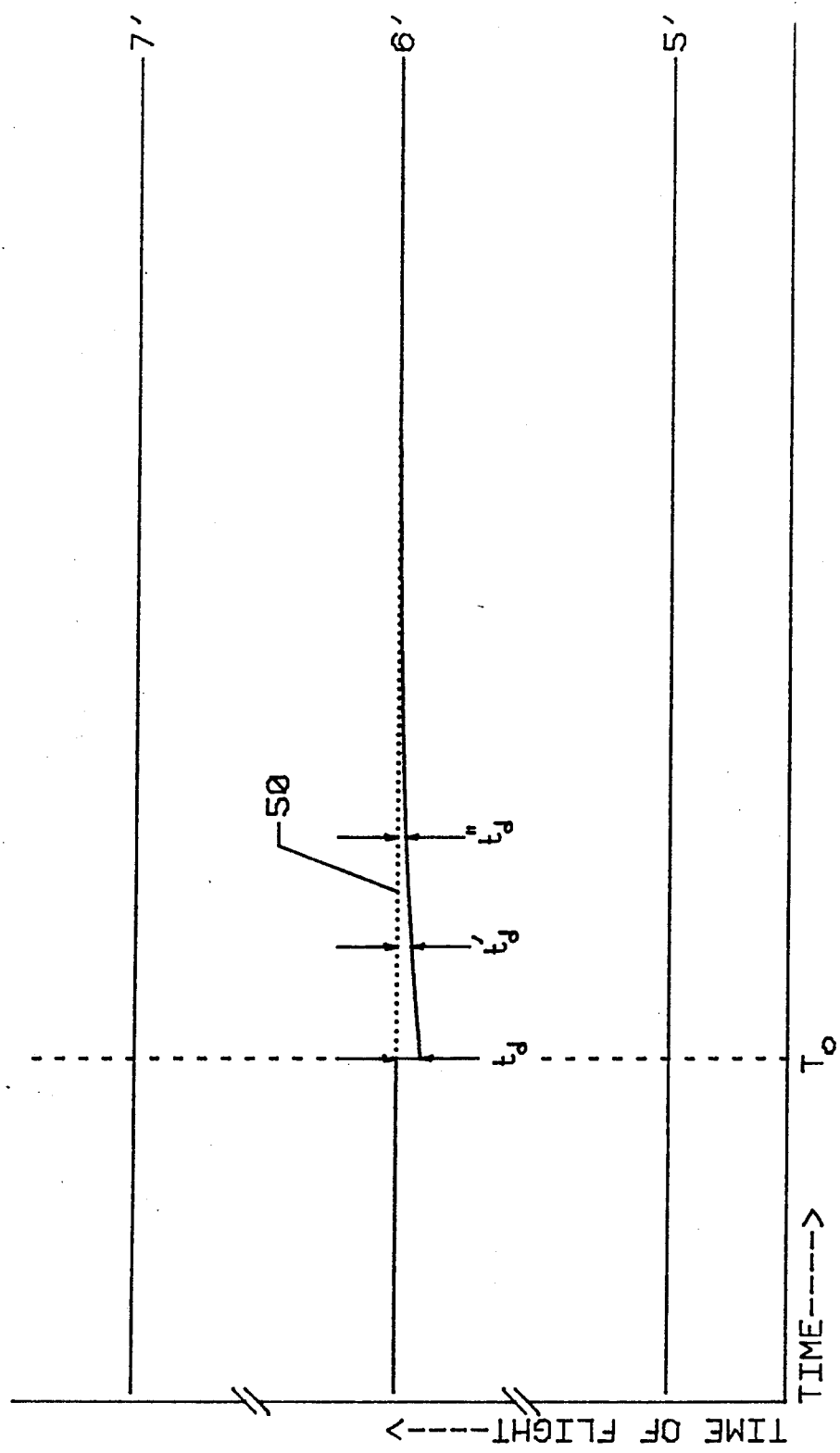
FIGS. 3-6 are charts illustrating certain characteristics of one embodiment of the invention.
Figure 4:
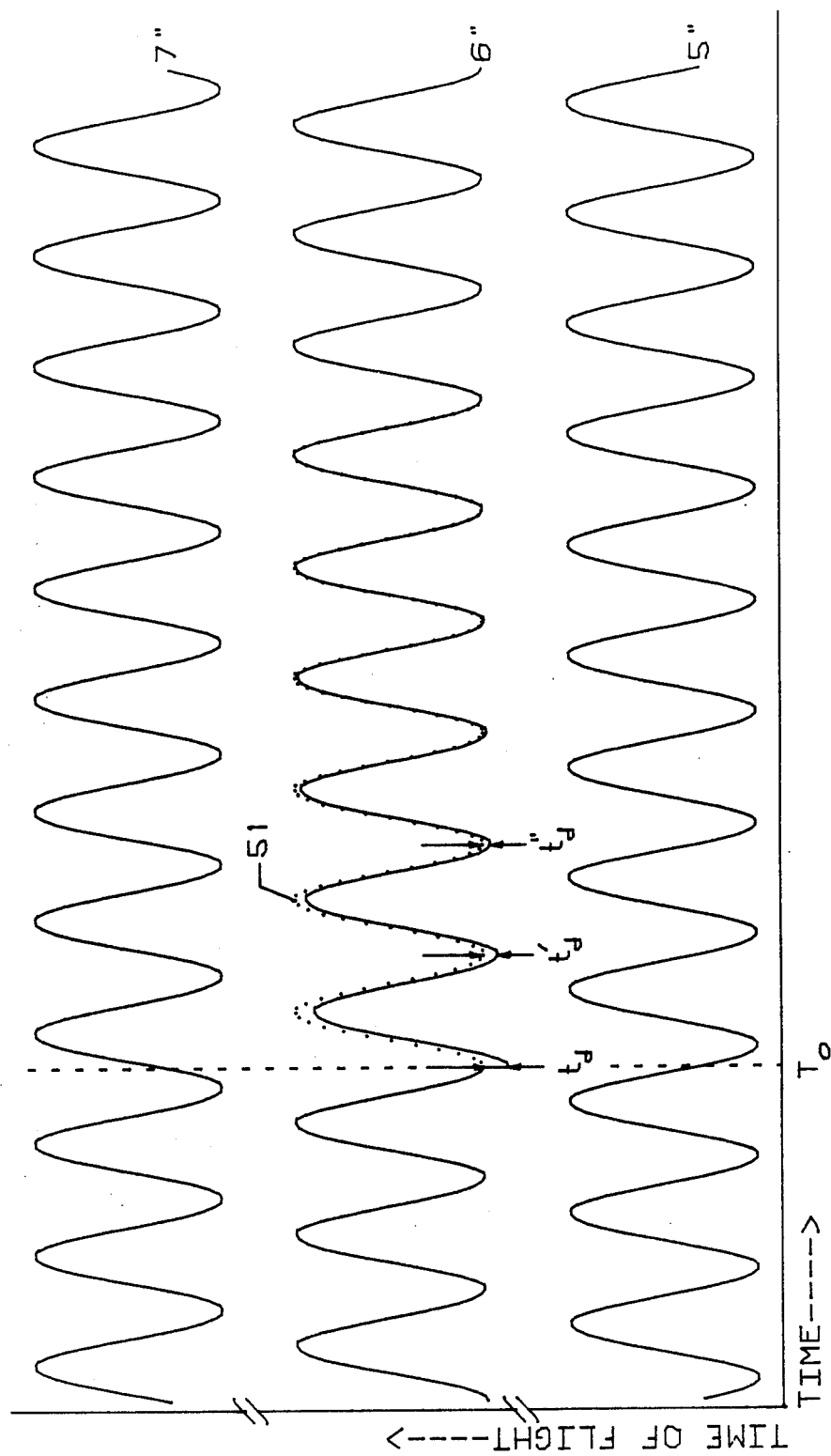

In FIGS. 3 and 4, the times of flight for the sense beam 6 and for the reference beams 5,7 are plotted as functions of time (on the abscissa) in two of many possible situations. For convenience sake, the reference beam 5's time of flight is shown below that of beam 6 which is in turn below that of beam 7 in these figures. In practice, the times of flight of the three beams would often be close in value.

Processing of the Information Obtained

The present invention uses the time variations of the times of flight of the three beams, while the system is setting up for a measurement, to determine the parameters of a model which will be used to reduce interference during the measurement.

In the time domain in the left quarter of the graphs, the computer monitors the times of transit of the reference beams and of the sense beam, which is at this time unperturbed. During this period, the computer develops the parameters of the model, from which it can predict the variations in the time of flight of the unperturbed sense beam, from measurements of the variations in the times of flight of the reference beams only.

The correctness of the parameters in the model can be assessed by the algorithm, by comparison of its predictions with the time of flight values for the sense beam measured without operation of the perturbing field. By operating the system without the perturbing field, the algorithm can assess and improve the values of the parameters it obtains until some pre-set degree of accuracy has been obtained.

When the parameters of the model are adequately known, the computer triggers a perturbing field burst. Although not truly instantaneous, the perturbing field burst is short enough to appear instantaneous on the time scale used in FIGS. 3-6. The instant at which said burst occurs is designated at $T_o$.

Following $T_o$, the computer continues to monitor the times of transit of the reference beams and, inserting this data in its model, it derives a hypothetical curve (such as 50 or 51 in FIGS. 3 and 4 respectively) showing, as a function of time, the variations which would have been expected to occur in the time of flight of the sense beam if no perturbation had taken place. Simultaneously, the computer also monitor the times of flight actually measured for the sense beam and stores a series of them in memory. Finally the computer determines the effect of the perturbation on the time of flight of the sense beam by subtracting, at appropriately chosen times, the time of flight values given by said hypothetical curve from the actually measured time of flight values. These sense beam time of flight differences are the desired signals.

Special Case I: Tissue at rest or motion not of effect

The simplest possible situation (FIG. 3) occurs when the time variations in the times of flight of the reference beams 5,7, as well as the time variation before $T_o$ in the time of flight of the sensing beam 6, are all zero; and the time of flight of the sensing beam 6 returns to its initial value after the perturbing heating effect (produced by the perturbing field) "dies out". The curves depicting the times of flight of the reference beams 5,7 are the straight lines 5' and 7', respectively, while the variation of the time of flight of the sensing beam 6 is represented by the partly straight, partly curved line 6'. The jump in this curve at $T_o$ represents the initial effect of the perturbing field burst, and the gradual return of this curve to its initial level represents the "dying out" of said effect. This situation is interpreted to mean either (i) the tissue is at rest, or (ii) such motions as may exist do not affect the times of flight of the beams 5,6,7. The variation of the hypothetical model of the time variation which would have occurred in the time of flight of the sense beam 6 (if there had been no perturbing field burst) is the dotted line segment 50 which joins the two straight portions of line 6'. The initial time of flight change $t_d$, used to find the "P-factor" (defined below) is the height of the jump in line 6'. Later time of flight differences, such as $t'_d$ and $t''_d$, which are used in finding the D-factor, are the differences between the solid and dotted lines at later times. Note that it is the time of flight difference which is the parameter of significance.

The "P-factor" is the perturbation factor, a parameter dependent upon the tissue being examined and affected, in a complex fashion, by the frequency of the perturbing field and the temperature of the tissue. It is given by the equation:

$$P = \alpha \left( \frac{\partial V}{\partial T} \right) / C\rho V^2;$$

where $\alpha$ is the amplitude absorption coefficient of the tissue at the perturbing field frequency, V is the velocity of sound in the tissue, $\rho$ is the density of the tissue, C is the specific heat of the tissue, and $$\frac{\partial V}{\partial T}$$

is the temperature coefficient of the velocity of sound in the tissue at its ambient temperature (See U.S. Pat. No. 3,771,355 at column 12, line 67 to column 13, line 60.) The "D-factor" is related to the rate of cooling of the tissue, see U.S. Pat. No. 3,771,335 at column 15, line 59 to column 16, line 24.

Special Case II: Periodic motion

FIG. 4 shows a slightly more complicated situation wherein the times of flight for all three beams have more or less similar periodic time variations. The times of flight for the reference beams 5,7 are represented by curves 5" and 7". The time of flight for the sense beam 6 is represented by curve 6". The jump in curve 6" at $T_o$ represents the initial effect of the perturbing field burst, and the gradual return of this curve to its initial periodic pattern represents the "dying out" of that effect. This situation is interpreted to mean that the tissue motions are periodic, without any break in the pattern at $T_o$. The curve depicting the output of the hypothetical model of the time variation which would have occurred in the time of flight of the sense beam 6, if there had been no perturbing field burst, is the dotted segment 51. The initial time of flight change, $t_d$, which is used in finding the P factor, is the height of the jump in curve 6". Later time of flight changes, such as $t'_d$ and $t''_d$, which are used in finding the D-factor, are the differences between the solid and dotted curves at later times.

Alternatively, the differences between the measured sense beam times of flight (curve 6″) and the hypothetical unperturbed times of flight (curve 51) may be plotted as in FIG. 4.1. Then values of $t_d$, $t'_d$, $t''_d$, etc. may be determined from this curve.

General Case: Random Motion

There are two components of the noise which affect the TAST system. Type 1 noise consists of periodic motions (not necessarily simple in shape) of the subject which lead to periodic variations in the time of flight (e.g., as in FIG. 4). Type 2 noise consists of cycle-to-cycle variations in the shape and period of the type 1 noise. An algorithm to remove type 1 noise is relatively simple and produces an output comparable to the curve of FIG. 4.1 (See, for example, special case II, supra.)

Figure 5:
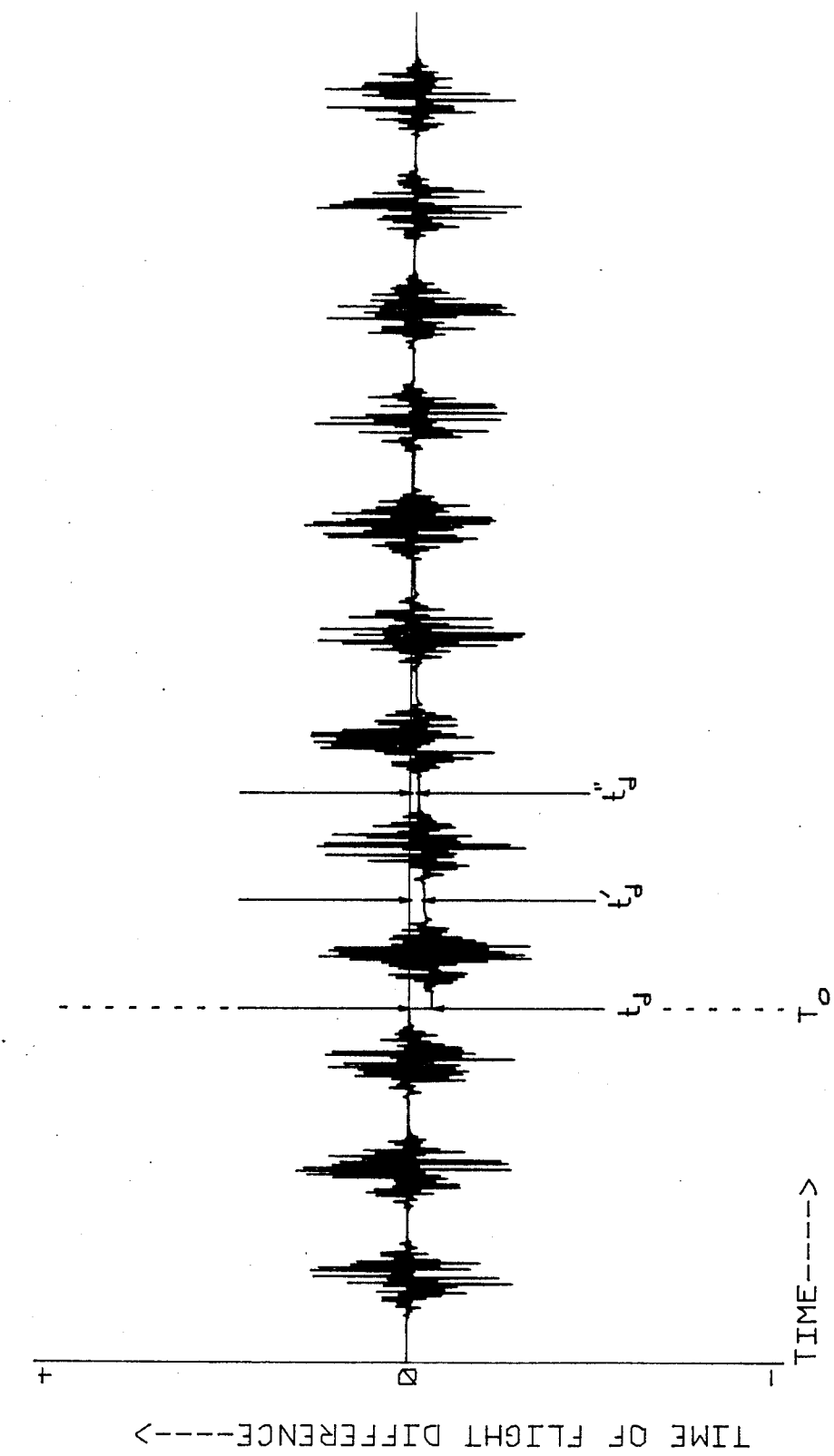

FIG. 5 shows the results of type 2 noise added to the signal fed to the algorithm. Note that there are times when the output is so noisy that the data is buried. At other times the noise remaining after processing by the algorithm is negligible and the signal of interest can easily be seen as being comparable to the curve of FIG. 4.1. This apparent lack of noise occurs because the waveform is repeating accurately at times when measurements can be made. Measurements should be taken continuously, but once the "windows" in the noise have been found, only that data falling within the window is used. The algorithm must indicate the times at which its prediction is valid, and then the curve can be reconstructed from the points available.

One can improve the algorithm's function by giving it information about the momentary periodicity of the motions during the times of interest. This data can be generated by means of standard cardiac, plethysmographic, respiratory and/or stethoscopic sensors. The algorithm can then distort its time scale to fit with the varying periodicity of the patient's body functions.

Figure 6:
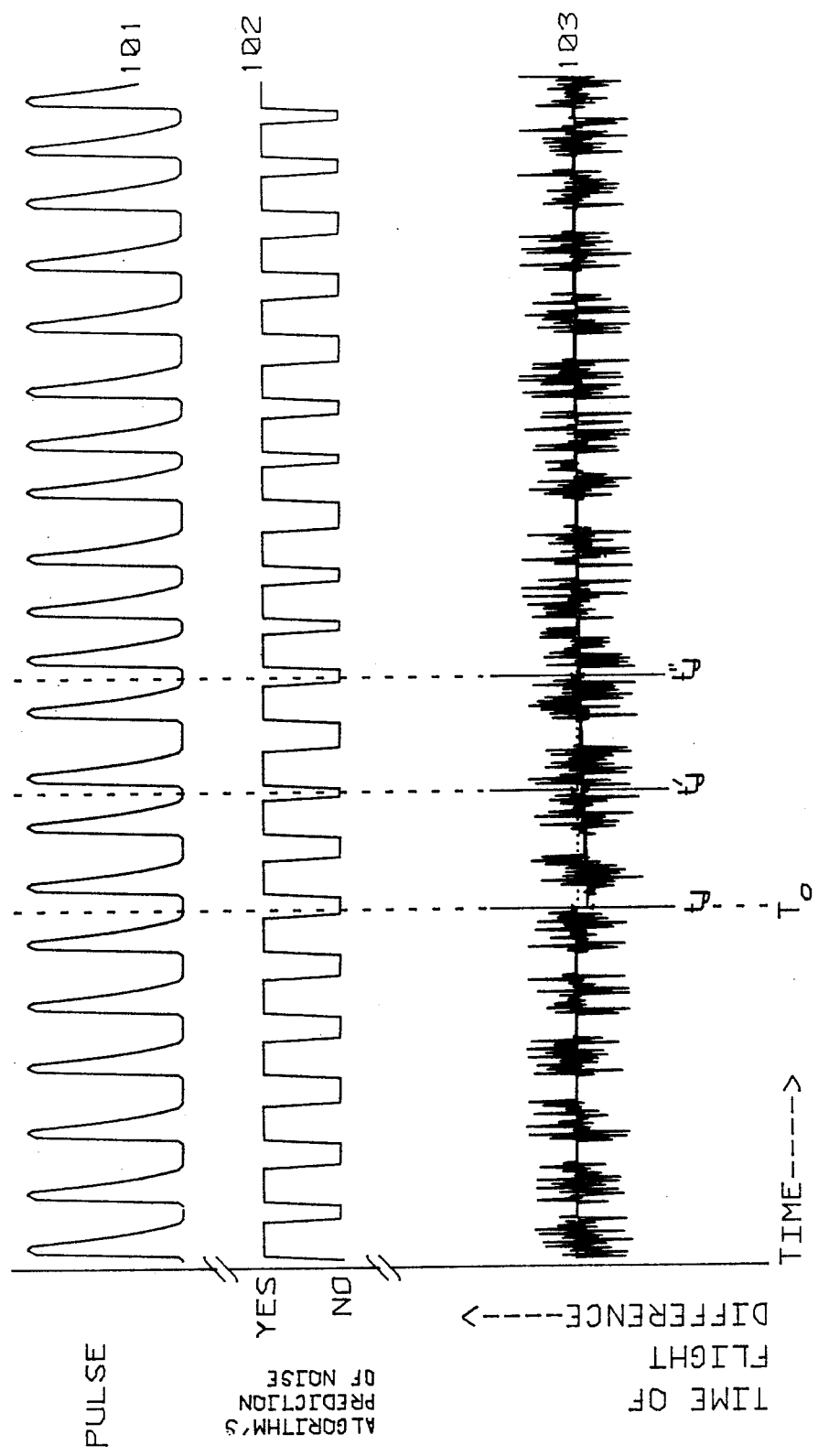

Such a situation is shown in FIG. 6. Curve 101 displays the output of a plethysmographic or stethoscopic pulse sensor. Curve 103 is comparable to the curve of FIG. 5. Curve 102 is the algorithm's prediction for type 2 noise level. Said prediction determines when the system chooses the time $T_o$ to occur, and when $t_d$, $t'_d$, $t''_d$, etc. are to be measured.

What is claimed is:

1. A system for ultrasonic inspection of a living substance including
    perturbing means to perturb an interior volume of said substance by ultrasonic waves, said perturbing means including a first transducer, a first oscillator connected to said first transducer, and means to cause the waves produced by said first transducer to produce a heated focal region;
    means to produce a collimated ultrasonic sense beam directed through said focal region and means to produce at least one reference beam directed near said focal region but not through it, said sense beam means and said reference beam means including an ultrasonic transmitting transducer to produce its respective collimated beam, a reference oscillator which is a source of continuous oscillations of ultrasonic frequency, and gating means connected between said source and said transducer to produce bursts of oscillations which are fed to its said transducer, thus producing discrete trains of ultrasonic waves;
    at least two ultrasonic receiving transducers each positioned to receive respectively said sensing beam and said reference beam and at least two phase comparison circuits with one phase comparison circuit being connected to each of said receiving transducers and to the reference oscillator for its respective transmitting transducer to respond to time of flight changes in the respective beams caused by transmission of the sense beam through said focal region with said heating compared to transmission of the sense beam through said focal region without said heating; and
    means to compare time of flight changes in the sense beam and said reference beam in order to lessen the adverse effects of tissue movement of the living substance during the measurement.

2. An instrument as in claim 1 and also including at least two changeable phase shifters, each phase shifter connected between said reference oscillator and one of said phase comparison circuits.

3. A system for ultrasonic inspection of a living substance including
    perturbing means to perturb an interior volume of said substance by ultrasonic waves, said perturbing means including a first transducer, a first oscillator connected to said first transducer, and means to cause the waves produced by said first transducer to produce a heated focal region;
    means to produce a collimated ultrasonic sense beam one portion of which is directed through said focal region and the diameter of which exceeds the diameter of said focal region, said sense beam means including an ultrasonic transmitting transducer to produce said collimated beam, a reference oscillator which is a source of continuous oscillations of ultrasonic frequency, and gating means connected between said source and said transducer to produce coherent bursts of oscillations which become discrete trains of ultrasonic waves from said transducer;
    at least two ultrasonic receiving transducers each positioned to receive a different portion of said sense beam, one portion being that part of said sense beam which has passed through the focal region and the other portion being part of said sense beam which has passed near said focal region but not through it;
    and at least two phase comparison circuits with one phase comparison circuit being connected to each of said receiving transducers and to the reference oscillator to respond to time of flight changes in the respective portions of the sense beam caused by transmission of one portion of the beam through said focal region with said heating compared to transmission of said portion of the sense beam through said focal region without heating; and
    means to compare time of flight changes in the different portions of said sense beam in order to lessen the adverse effects of tissue movement of the living substance during the measurement.

4. A method for ultrasonic inspection of a living substance including
    perturbing an interior volume of said substance by exciting waves from a first transducer controlled by a first oscillator to produce a heated focal region;
    producing a collimated ultrasonic sense beam directed through said focal region and at least one collimated ultrasonic reference beam directed near said focal region but not through it, each of said sense and reference beams being produced by an ultrasonic transmitting transducer, a reference oscillator which is a source of continuous waves of ultrasonic frequency, and gating means connected between said source and said transducers to produce bursts to oscillations which produce discrete trains of ultrasonic waves at said transmitting transducers;

receiving said sense beam and said reference beam by at least two ultrasonic receiving transducers, comparing the phases of the received sense beam and the received reference beam each with a time of flight comparison circuit, a time of flight comparison circuit being connected to each of said receiving transducers and to the reference oscillator, thereby responding to the time of flight changes in the sense beam caused by transmission through said focal region with said heating compared to transmission through said focal region without said heating; and comparing the time of flight changes in the sense and reference beams in order to lessen the adverse effects of tissue movement of the living substance during its measurement.

* * * * *

UNITED STATES PATENT OFFICE
CERTIFICATE OF CORRECTION

Patent No. 4,431,008              Dated February 14, 1984

Inventor(s) James F. Wanner and Clinton D. Janney

It is certified that error appears in the above-identified patent and that said Letters Patent are hereby corrected as shown below:

Column 4, line 32, "20 22" changed to -- 20-22 --;

Column 4, line 32, "outputs" changed to -- inputs --

Signed and Sealed this

Twenty-sixth Day of June 1984

[SEAL]

Attest:

GERALD J. MOSSINGHOFF

Attesting Officer        Commissioner of Patents and Trademarks